United States Patent [19]

Regnault et al.

[11] 4,241,089
[45] Dec. 23, 1980

[54] FEEDSTUFF FOR LIVESTOCK AND MANUFACTURING THEREOF

[75] Inventors: Alain Regnault, Par Ornet; Jean-Pierre Sachetto, St. Julien-en-Genevois, both of France

[73] Assignee: Battelle Memorial Institute, Carouge, Switzerland

[21] Appl. No.: 913,834

[22] Filed: Jun. 8, 1978

[30] Foreign Application Priority Data

Jun. 10, 1977 [CH] Switzerland ............... 7159/77

[51] Int. Cl.³ ............................................. A23K 1/16
[52] U.S. Cl. ........................................ 426/2; 426/69; 426/630; 426/635; 426/658
[58] Field of Search .................. 426/69, 2, 630, 635, 426/658; 536/53, 22

[56] References Cited

U.S. PATENT DOCUMENTS

| | | | |
|---|---|---|---|
| 2,612,497 | 9/1952 | Meijer | 536/22 X |
| 2,748,001 | 5/1956 | Anderson et al. | 426/69 |
| 3,677,767 | 7/1972 | McNeff et al. | 426/2 |
| 3,873,733 | 3/1975 | Moore | 426/69 |
| 3,873,734 | 3/1975 | Higgins et al. | 426/69 |
| 4,044,156 | 8/1977 | Diner et al. | 426/69 |

Primary Examiner—Robert A. Yoncoskie
Attorney, Agent, or Firm—Philip M. Dunson; P. A. Chopard

[57] ABSTRACT

Feedstuff for livestock containing essentially carbohydrates (starches and cellulose based products) and glucosylurea of more than 90% purity. The glucosylurea is obtained by the condensation under acidic conditions of urea and glucose and the addition of 30–50% water which results, after final concentration and cooling, in the crystallization of pale yellow glucosylurea.

5 Claims, No Drawings

FEEDSTUFF FOR LIVESTOCK AND MANUFACTURING THEREOF

The present invention concerns a feedstuff for cattle based on carbohydrates and a urea derivative.

The invention also concerns a process for manufacturing this feedstuff and, especially, the urea derivative which is a part thereof.

The feedstuff according to the invention provides a more favorable assimilation of the nitrogen combined with the urea and, simultaneously, an improved assimilation of the carbohydrates present in the feedstuff, all this as compared with existing products.

It is known that ruminants need in order to grow normally, as do other living beings, a well-balanced diet comprising, particularly, adequate proportions of carbohydrates and nitrogen containing products. It is also known that such animals are capable of digesting and assimilating a significant proportion of carbohydrates in the form of cellulose-based products.

Moreover, due to the presence of some microorganisms in their digestive tract, ruminants are able to synthetize, from ammonia and sugars, the amino-acids required for building-up their organic tissues. This ammonia can be generated in the rumen of ruminants by the enzymatic hydrolysis of nitrogen compounds, especially from urea mixed with the fodder. However, the rate of ammonia formation from urea in the stomach of ruminants is much faster than the rate of its use by the mircroorganisms for the synthetis of the protein which generate said amino-acids. Consequently, mixing urea with the fodder may in some cases lead to the liberation, in the digestive tract of the animals, of a temporary excess of ammonia and hence cause a poisoning hazard for the latter.

In order to remedy these drawbacks, it has become necessary to replace urea by some derivatives thereof the slower hydrolysis of which enables a more progressive release of ammonia. Urea compounds which have particularly favorable properties in this respect are the glycosyl-derivatives. Effectively, by their decomposition, these compounds simultaneously release ammonia and the energy elements (carbohydrates) necessary for the life of the animals and for the build-up of their tissues.

Thus, U.S. Pat. No. 2,748,001 (1956) discloses the preparation of an animal feed-supplement which comprises mixing (while heating up to about 80° C.) the following ingredients: Molasses 50% or more; urea 2–20%; water 25–35%; $H_3PO_4$ 0.27–2%; oligo-elements in traces; pH 4–4.75.

Although it is not indicated in the patent that glucosylurea will form in such a mixture, this formation is probable since the urea of the feedstuff is better assimilated by the animals than when provided separately.

Russian Pat. No. 264,155 (1970) discloses the manufacturing of a feedstuff for animals which contains, for instance, glycosylureides. This feedstuff is obtained by the acid hydrolysis (HCl or $H_2SO_4$), under heating, of vegetal refuses, molasses or starches, then urea is added in the ratio of 3 moles per mole or sugar and the mixture is heated for 45–50 hrs to 55°–65° C. Thereafter, the acid is neutralized with sodium hydroxide. One of the feedstuffs manufactured accordingly contains 14.2% flucosylurea, 10% urea and 27.4% sugars.

Russian Pat. No. 302,093, similar to the previous one, further discloses that the formation of the feedstuff (which contains the following glycosylureas: mannosylurea, xylosylurea and glucosylurea) is accelerated by the addition of $H_3PO_4$. This acid has also the property of fixing the excess of urea in the form of the phosphate which does not have the same drawbacks, dietwise, as free urea.

U.S. Pat. No. 3,677,767 discloses in details the delaying effect on the release of ammonia provided by the use, in fodders, of compounds of urea and saccharides and it also discloses a feedstuff for animals and a process for its preparation. In this process, a mixture about 1:1 of molasses and urea is heated above 65° C. and at pH below 4 ($H_2SO_4$ or $H_3PO_4$) for a period sufficient for having the conversion ratio of the total "protein equivalent" into a "protein equivalent" non-decomposable by urease to exceed 20%. This reference further indicates, although without specifying which ones, that acids others than $H_3PO_4$ or $H_2SO_4$ are usable in this process.

French Pat. No. 2,265,286 [75/09723 (1975), priority 4.1974]discloses an animal feedstuff containing a reacted mixture of urea, molasses and acid, at least 51% of the latter consisting of HCl.

All the feedstuff products provided by the cited prior-art, in which the glucosylureas are in the form of crude solutions or heavy sirups, enable a more favorable assimilation of the urea (of glucosylureas) as compared to the assimilation of an equivalent of urea which would be provided in the fodder in chemically free form. However, it is disclosed nowhere that such products may simultaneously have the property of improving and increasing the assimilation of the cellulosic carbohydrates also possibly present in such feedstuff.

The feedstuff according to the invention is characterized by the fact that the urea derivative is a solid glucosylurea of at least 90% purity and having a total of unbound glucose and urea not exceeding 10%.

It was noticed with surprise that the incorporation of such grade of glucosylurea into a carbohydrate based fodder resulted not only in a more favorable assimilation by the ruminants of the nitrogen of the bound urea but also in a markedly increased assimilation of the cellulosic and hemicellulosic carbohydrate fraction of this feedstuff.

As general carbohydrates, the present feedstuff can contain starches, for instance maize, barley or other cereals, fecula, etc . . . preferably in proportions comprised between about 30 and 70%. It can also comprise about 20 to 50% of cellulose-based products such as straw, hay, vegetal roughage, oil-seed cakes, etc . . . The remainder of the feedstuff comprises the solid glucosylurea in quantities of approximately 2 to 10%, which is under the form of odorless white crystals, slightly sweet tasting and, possibly, other additives such as water, binders, premixes, fats, flavors, etc . . . Such additional materials are abundantly described in the prior-art literature (see for inst. U.S. Pat. Nos. 3,677,767; 2,748,001; 3,753,722; 3,684,518 and related publications).

Evidently, the compositions above are given for illustrative purpose only and, if required, the respective concentration of the ingredients can be outside the above stated limits.

The process for the preparation of the feedstuff according to the invention which consists in mixing together the various constituents mentioned above with the solid glucosylurea is characterized by the fact that the latter is obtained as follows: One equivalent of glucose is heated together with one equivalent of urea to a temperature comprised between about 60° and 70° C. in the presence of a mineral acid as dehydrating agent and, thereafter, there is added about 30–50% of water on the basis of the total weight of the mixture which will result, after concentration and cooling, in the crystallization of rather pure glucosylurea.

As convenient acids, $H_2SO_4$, $H_3PO_4$ or other strong acids can be used.

This process must be distinguished from that of U.S. Pat. No. 2,612,497 which discloses the preparation of glycosylurea from glucose, galactose, arabinose, mannose, fructose and hexose precursors, namely polysaccharides and disaccharides such as sucrose, maltose and lactose. It more particularly discloses the obtention of glucosylurea and glucosylthiourea by using, as a carbohydrate source, either pure glucose, or cane-sugar and, as condensation agents, $H_2SO_4$ or $H_3PO_4$. The operating conditions are: 60°–100° C.; acid not exceeding 20%; water no more than 20%. However, this process of the prior-art leads to the precipitation of a waxy, relatively impure glucosylurea (which must be further purified before use) whereas the present process gives a product with more than 90% purity and which can used as such in the present fodder of the invention.

The following examples illustrate the invention in a detailed manner.

EXAMPLE 1

Preparation of a feedstuff and its use for feeding ruminants

A feedstuff (B) according to the invention and a control feedstuff (A) without glucosylurea were prepared by mixing the following ingredients in a mill and, thereafter, by granulating the mixes with an appropriate machine.

The compositions are as follows:

| Ingredients | Parts by weight (A) | (B) |
|---|---|---|
| Finely ground maize | 54.5 | 54.5 |
| Barley | 10.0 | 6.5 |
| Chopped straw | 25.0 | 25.0 |
| Marc of fruit | 5.0 | 5.0 |
| Fat | 1.5 | 1.5 |
| Urea | 1.5 | — |
| Glucosylurea | — | 5.0 |
| Binder | 1.5 | 1.5 |
| Premix | 1.0 | 1.0 |

It should be remarked that, equivalentwise, 5.0 g of glucoslyurea represents 1.4 g of free urea. The amount of equivalent urea in sample (B) was therefore slightly less than in control (A).

The approximate nutritional values calculated for (A) and (B) were: Digestible energy 3.02 Mcal/kg; raw protein 11,3%.

Two groups each of ten sheep were fed, one group with feedstuff (A) and the other with feedstuff (B), respectively, for 3 weeks and it was noticed afterwards that the average weight increase of the animals was 2% in the case of feedstuff (A) and 3.5% in the case of feedstuff (B) containing the glucosylurea. The difference in weight gain in stuff (B) relative to (A) is therefore 75%. This figure may be compared to similar figures obtained with steers in the case of feed supplements containing glycosylureides from the prior-art. For instance, in the case of hydrolyzed starch glucosylurea (see U.S. Pat. No. 4,044,156) where the weight gain over a non glucosylurea diet was 20% or the so called "molasses-urea" mixtures (see U.S. Pat. No. 3,677,767) where the gain over a free urea diet was about 6.7% and over a control with natural proteins only was about 7.5%.

Futhermore, for the whole duration of the experiment, samples of rumen juice were removed from some of the sheep and analyzed. The analyses first concerned the pH changes and the ammonia content, which values constitute a direct measurement of the degradation rate of the nitrogen containing ingredients of the feedstuffs. The results are recorded in Tables I and II below as a function of the time elapsed after eating the feedstuffs.

TABLE I

| | Change in pH | |
|---|---|---|
| time (min) | (A) | (B) |
| 0 | 7.30 | 7.08 |
| 20 | 7.16 | 6.78 |
| 40 | 6.98 | 6.55 |
| 60 | 6.70 | 6.37 |
| 120 | 5.88 | 6.18 |
| 240 | 6.10 | 6.04 |
| 360 | 6.53 | 6.16 |
| 480 | 6.80 | 6.40 |

TABLE II

| | Variation of ammonia content (%) | |
|---|---|---|
| time (min) | (A) | (B) |
| 0 | 4.37 | 6.43 |
| 20 | 33.72 | 11.88 |
| 40 | 26.54 | 12.02 |
| 60 | 20.80 | 10.32 |
| 120 | 4.05 | 9.53 |
| 240 | 0.93 | 3.33 |

From the results of Tables I and II, it can be seen that the release of ammonia from the feedstuffs is slower in the case of sample (B) containing the glucosylurea than for samples (A) containing the free urea.

Analytical measurements also concerned the formation, in the course of digestion time, of volatile acids. This measure is important because it correlates directly with the rate of degradation for the carbohydrates and, consequently, to the degree of assimilability thereof. The results are recorded below in Table III with regard to feedstuff (B) and in Table IV with regard to feedstuff (A).

TABLE III

| | Volatile acids mM/l: feedstuff (B) | | | | | |
|---|---|---|---|---|---|---|
| | Time after meal (min) | | | | | |
| Acids | 0 | 60 | 120 | 240 | 360 | 480 |
| acetic | 22.72 | 37.44 | 47.02 | 55.14 | 45.71 | 43.09 |
| propionic | 8.26 | 19.80 | 26.97 | 31.51 | 27.05 | 25.47 |
| iso-butyric | 0.71 | 0.49 | 0.52 | 0.49 | 0.46 | 0.38 |
| butyric | 4.01 | 9.04 | 12.03 | 14.91 | 8.05 | 7.30 |
| iso-valeric | 0.91 | 0.50 | 0.37 | 0.59 | 0.49 | 0.57 |
| valeric | 0.67 | 1.43 | 1.31 | 1.91 | 0.94 | 0.79 |
| caproic | 0.24 | 0.28 | 0.45 | 0.61 | 0.35 | 0.20 |
| Total | 37.51 | 68.96 | 88.67 | 105.14 | 83.02 | 77.78 |

TABLE IV

| | Volatile acids mM/l: feedstuff (A) | | | | | |
|---|---|---|---|---|---|---|
| | Time after meal (min) | | | | | |
| Acids | 0 | 60 | 120 | 240 | 360 | 480 |
| acetic | 16.87 | 36.69 | 45.88 | 39.52 | 35.40 | 32.26 |

TABLE IV-continued

| | Volatile acids mM/l: feedstuff (A) | | | | | |
|---|---|---|---|---|---|---|
| | Time after meal (min) | | | | | |
| Acids | 0 | 60 | 120 | 240 | 360 | 480 |
| propionic | 5.82 | 20.55 | 31.29 | 31.18 | 23.55 | 17.41 |
| iso-butyric | 0.52 | 0.43 | 0.40 | 0.38 | 0.39 | 0.49 |
| butyric | 1.75 | 4.86 | 8.22 | 9.03 | 8.12 | 6.51 |
| iso-valeric | 0.64 | 0.36 | 0.21 | 0.40 | 0.56 | 0.65 |
| valeric | 0.46 | 1.06 | 1.35 | 1.43 | 1.08 | 0.74 |
| caproic | 0.06 | 0.14 | 0.27 | 0.25 | 0.36 | 0.32 |
| Total | 26.11 | 64.08 | 87.61 | 82.17 | 69.45 | 58.36 |

The results of Tables III and IV are particularly surprising in view of the fact that feedstuff (B) contains only about 2% more starches than feedstuff (A); this is because, percentwise, the glucose moiety of the glucosylurea replaces part of the barley which, itself, is not pure starch. Therefore, it would be expected that the quantities of volatile acids formed in the course of the digestion of feedstuffs (A) and (B) should be roughly the same. Now, the above results show that this is not the case: the presence of the solid glucosylurea results in the formation of an average concentration of volatile acids significantly larger than in the presence of free urea: 84.6 versus 71.3 mM/1, respectively (i.e. +18.7% difference). It should be remarked that the increase in production of volatile acids does not occur immediately after meal but only 2–3 hrs afterwards. It can therefore be postulated that glucosylurea, or some of its components, stimulate the degradation of carbohydrates other than starches, i.e. the cellulose-based products. Further, although the average concentrations of acetic, propionic and butyric acid are all increased, the effect is the larger with acetic acid (45.3 versus 36.6 mM/1, i.e. +23.5%).

The glucosylurea used in the present example had the following physical characteristics:

| | |
|---|---|
| Moisture content | 1.2% |
| Total nitrogen | 13.55% |
| Free urea (titrated by urease) | 3.15% |
| Free glucose (titrated by glucose oxidase) | 2.3% |
| Purity | 94.55% |
| Urea equivalent | 25.6% |
| Protein equivalent | 6.25 × 13.55 = 84.66 g/100 g |
| Melting point | 198° C. (dec) |
| [α] | −16° ($H_2O$, C = 2%) |
| Aspect and taste | white, odorless, slightly sweet crystals. (Free urea is bitter) |

EXAMPLE 2

Preparation of crystallized glucosylurea

Glucose monohydrate (204 g) and water (60 ml) were placed in a 6 l beaker provided with a powerful stirrer and a heater stabilized by thermostat at 60° C.

After stirring 3 min, 680 g of urea were added. After 10 min at 60° C., the mass was molten as a thick syrup. Then, still under agitation, there were added a further 1836 g of glucose monohydrate in portion of about 200 g at approximately 10 min intervals. After this addition (1½ h), there was added a solution of 33 ml of 98% $H_2SO_4$ in 60 ml $H_2O$.

The mixture was agitated for 8 hrs at 68° C., then 2 l of $H_2O$ were added to the viscous mass. The pH was measured to be equal to 1. The heating was stopped, there were further added 67 g of $CaCO_3$ and the mixture was stirred overnight with 15 g of active charcoal whereby the temperature went down to room-temperature. The next day, the resulting syrup was filtered on a filter-paper, then it was concentrated under reduced pressure until crystals started to form. The pale yellow crystals were collected on a Büchner funnel and dried under vacuum in the presence of $P_2O_5$. First crop, yield 850 g, mp. 190° C. (dec). The mother-liquors from the first run were further concentrated and yielded, after crystallization a second crop of 1100 g of crystals of slightly deeper color; mp. 180°–200° C. after washing with boiling ethanol and drying over $P_2O_5$. The second crop was better than 90% pure and could be used directly for the preparation of the feedstuff of the invention. After 1 crystallization in water, it gave the following analytical results (crop 1 was not crystallized):

| Analysis Values for | 1st crop (uncrystallized) | 2nd crop (crystallized) |
|---|---|---|
| % N Total | 12.9 | 12.5 |
| % free urea | 3.1 | 2.2 |
| % free glucose | 2.3 | 1.3 |
| % purity | 94.6 | 96.5 |

We claim:

1. Feedstuff for livestock comprising about 90 to 95 percent by weight of carbohydrates and about 2 to 10 percent by weight of a urea derivative, the latter being a crystallized glucosylurea the purity of which is at least 90% and the total chemically unbound urea and glucose of which does not exceed 10% by weight.

2. Feedstuff according to claim 1, wherein the carbohydrates thereof comprise a) starches and b) cellulose and hemicelluloses and wherein the content of a) is 30 to 70% and the content of b) is 20 to 50%, all by weight of the feedstuff.

3. Feedstuff according to claim 2, further comprising at least one of the following additives: water, binders, premix vitamins, fats, flavors.

4. Process for the preparation of feedstuff according to claim 1 which consists in heating to about 60°–70° C. one equivalent of glucose with one equivalent of urea under stirring in the presence of a strong acid such as $H_2SO_4$ as a dehydrating agent, diluting with about 30–50% by weight of water, concentrating and cooling until crystals of 90–98 percent pure glucosylurea separate, collecting such crystals, and mixing them with carbohydrates.

5. Process for feeding ruminants which comprises supplying said ruminants with crystallized, better than 90% pure, glucosylurea, in a quantity of about 2 to 10 percent by weight, in a diet containing cellulose and hemicellulose products, said glucosylurea acting as a stimulant for the digestion and the assimilation of such products by the animals.

* * * * *